(12) United States Patent
Wilson et al.

(10) Patent No.: US 6,767,737 B1
(45) Date of Patent: Jul. 27, 2004

(54) STEM CELLS BEARING AN FGF RECEPTOR ON THE CELL SURFACE

(75) Inventors: E. Lynette Wilson, New York, NY (US); Patricia E. Burger, Cape Town (ZA)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/386,228

(22) Filed: Aug. 31, 1999

Related U.S. Application Data

(60) Provisional application No. 60/098,480, filed on Aug. 31, 1998.

(51) Int. Cl.[7] ............................................. C12N 5/00
(52) U.S. Cl. ......................... 435/325; 435/366; 435/372
(58) Field of Search ................................. 435/325, 372, 435/366

(56) References Cited

U.S. PATENT DOCUMENTS

| | | | |
|---|---|---|---|
| 5,166,065 A | * | 11/1992 | Williams et al. |
| 5,670,372 A | * | 9/1997 | Hogan |
| 5,690,926 A | | 11/1997 | Hogan |
| 5,843,780 A | * | 12/1998 | Thomson |

OTHER PUBLICATIONS

Redwine et al., "In Situ Expression of Fibroblast Growth Factor Receptor by Oligodendrocyte Progenitors and Oligodendrocytes in Adult Mouse Central Nervous System", *Journal of Neuroscience Research*, vol. 50, pp. 229–237, (1997).

Ratajczak et al., "Effect of basic (FGF–2) and acidic (FGF–1) fibroblast growth factors on early haemopoietic cell development", *British Journal of Haematology*, vol. 93, No. 4, pp. 772–782, (1996).

Burger et al., "Isolation and characterization of a CD34+ population that expresses fibroblast growth factor receptors", *Blood, 40th Annual Meeting of the American Society of Hematology*, vol. 92, No. 10, pp. 56A.

Ratajczak et al., "An improved serum free system for cloning human "pure" erythroid colonies. The role of different growth factors and cytokines on BFU–E formation by the bone marrow and cord blood CD34+ cells", *Folia Histochemica Et Cytobilogica*, vol. 36, No. 2, pp. 55–60, (1998).

Gabrilove et al. "Stem cell factor and basis fibroblast growth factor are synergistic in augmenting committed myeloid progenitor cell growth", *Blood*, vol. 83, No. 4, pp. 907–910, (1994).

* cited by examiner

*Primary Examiner*—Leon B. Lankford, Jr.
(74) *Attorney, Agent, or Firm*—Browdy and Neimark

(57) ABSTRACT

A composition of substantially purified pluripotent stem cells are positive both for fibroblast growth factor receptor (FGFR) and a phenotype indicative of a primitive state, such as $CD34^+$, $CD34^-lin^-$, $Thy-1^+$, $AC133^+$ or $c-kit^+$. The state of being an embryonic stem cell is also a phenotype indicative of a primitive state. This population may be further defined by the subpopulations thereof which have another marker thereon indicative of endothelial cells, such as $TIE-1^+$, $TEK^+$, $CD31^+$, $VE-Cadherin^+$ or $VEGFR^+$ or indicative of stromal cells, such as $STRO-1^+$.

23 Claims, 6 Drawing Sheets

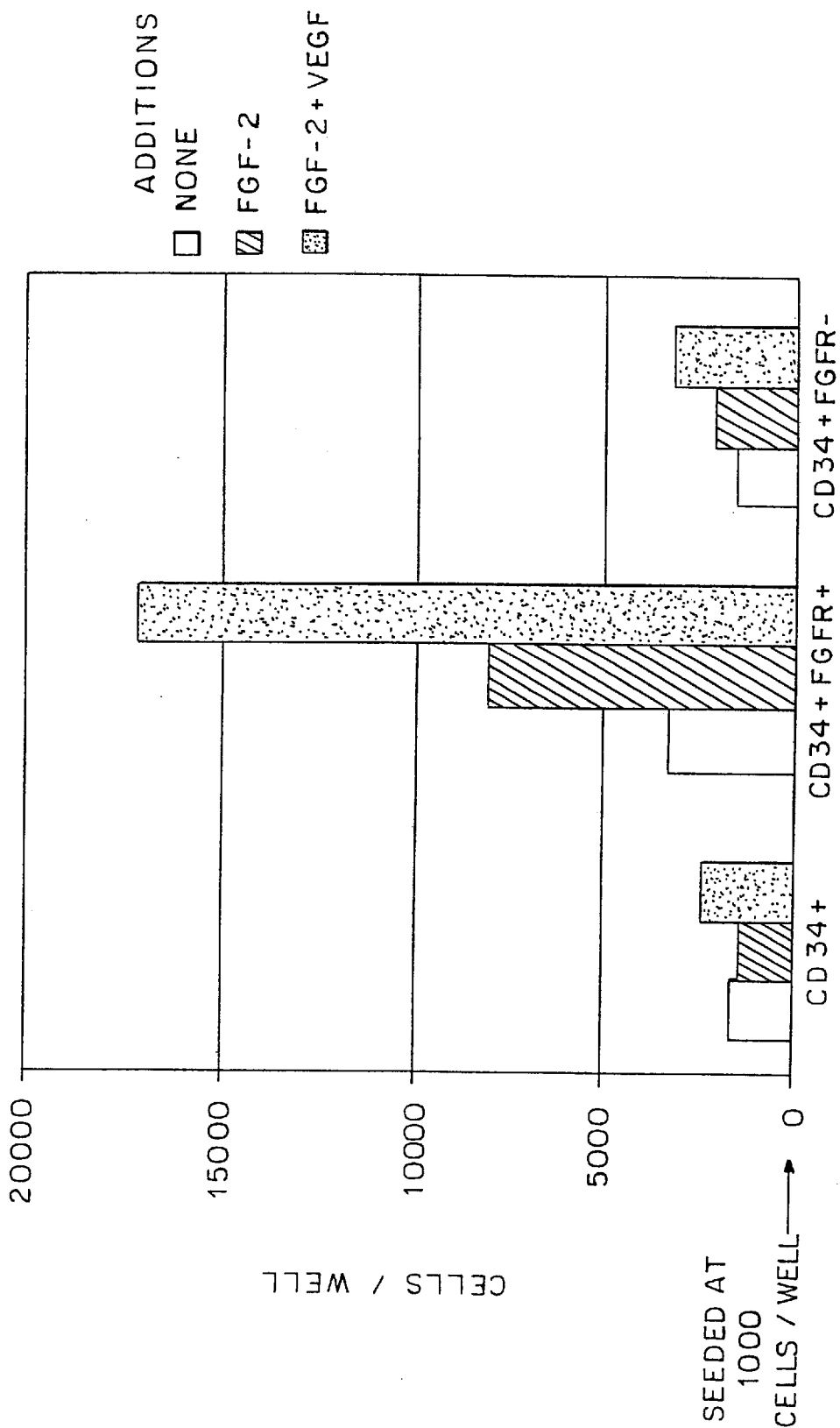

STEM CELLS BEARING AN FGF RECEPTOR ON THE CELL SURFACE

CROSS-REFERENCE TO RELATED APPLICATIONS

The present application claims benefit of the effective filing date of U.S. provisional patent 60/098,480, filed Aug. 31, 1998, the entire contents of which are hereby incorporated by reference.

GOVERNMENT LICENSE RIGHTS

The experiments or research performed in this application were supported in part by the National Institutes of Health, grant no. R01-DK48728. As such, the U.S. Government has certain rights in the invention.

FIELD OF INVENTION

The present invention is directed to a new phenotype of stem cells which contain a fibroblast growth factor receptor (FGFR) on the cell surface thereof and further have a phenotype indicative of a primitive state. The present invention is further directed to subpopulations thereof having a phenotype indicative of endothelial or stromal cells.

BACKGROUND OF THE INVENTION

The ability of tissues and organs to develop, remodel, regenerate, and repair depends on the existence of stem cells (also known as progenitor cells) that, upon division, form more differentiated progeny. Stem cells have been found in the epidermis, the intestinal epithelium, and the hematopoietic system. There is mostly indirect evidence of stem cells in mesenchymal tissues. In vivo and in vitro studies have provided evidence of osteogenic precursor cells in bone marrow and other stromal cell preparations. However, the identity of cells in these tissues and their relationship to cells with classical stem cell characteristics have yet to be established.

Endothelial cells are part of the normal bone marrow stroma. Long-term cultures of human bone marrow contain a complex mix of stromal cells including adipocytes, fibroblasts, endothelial cells, macrophages, and smooth muscle cells. Endothelial cells and hematopoietic cells are thought to be derived from the common progenitor cells, hemangioblasts.

Cell surface molecules on various types of cells, and particularly hematopoietic cells, are given a cluster of differentiation (CD) designation in which each CD molecule designation describes a surface molecule (marker) identifiable by a cluster of monoclonal antibodies that display the same cellular reactivity. CD designations are assigned at regularly held international workshops on human leukocyte differentiation antigens. For example, the CD19 marker is specific to B cells, and the CD33 marker is specific to myeloid cells. At the present time, it is not known how many of the markers associated with differentiated cells are also present on stem cells. One marker which has been indicated as being present on stem cells is CD34. However, this marker is also found on a significant number of lineage-committed progenitors. Other markers which are known or thought to be present primarily on stem cells, i.e., "primitive" markers, include AC133 (Yin et al, 1997; Buhring et al, 1999), Thy-1 (Murray et al, 1995) and c-kit (D'Arena et al, 1998).

It is known that a small number of circulating $CD34^+$ hematopoietic stem cells are present in peripheral blood. As the major source of $CD34^+$ hematopoietic stem cells in the adult is the bone marrow, the purpose of this small, circulating $CD34^+$ cell population is unknown. One explanation is that the bone marrow is "leaky", and the stem cells escape, circulate and return to the marrow. A second possibility is that the function of these circulating stem cells is to seed sites, such as the liver and the spleen, which can function as additional sites of hematopoiesis in a crisis.

The human $CD34^+$ hematopoietic population isolated from bone marrow, cord blood, and peripheral blood is a heterogeneous population that contains hematopoietic stem cells. Recent evidence indicates that circulating $CD34^+$ cells also contain endothelial stem cells, which may also circulate (Asahara et al, 1997; Nieda et al, 1997; Shi et al, 1998; Lin et al, 1998). Asahara et al (1997) have shown that $CD34^+$ cells isolated from the peripheral blood can be incorporated into the endothelium of ischaemic blood vessels of recipient animals. Purified umbilical cord blood $CD34^+$ cells also give rise to von Willebrand factor-expressing endothelial cells in vitro, providing additional evidence for a circulating progenitor endothelial cell (Nieda et al, 1997). In addition, bone marrow derived $CD34^+$ cells also contain a transplantable stromal stem cell (Prockop, 1997; Pereira et al, 1998).

Recently, convincing evidence has been presented (Goan et al, 1997) that human $CD34^+$ progenitor cells from peripheral blood or cord blood that were transplanted into NOD/SCID immunodeficient mice gave rise to human stromal cells. The human stromal cells expressed the endothelial cell-specific vascular endothelial growth factor (VEGF) receptor-2 (KDR) and von Willebrand factor, indicating that they were of endothelial origin. There is also recent evidence that infusion of whole bone marrow cells into recipient mice results in fibroblasts of donor origin in a number of non-hematopoietic tissues (Prockop, 1997; Pereira, 1998), indicating that stromal progenitor cells reside in the bone marrow. As CD34 has been shown to be expressed by bone marrow stromal precursor cells (Simmons et al, 1991), it is possible that these stromal progenitors reside in the bone marrow within the $CD34^+$ progenitor population.

The $CD34^+$ progenitor population is, therefore, a heterogeneous fraction that may include precursor cells of the hematopoietic, endothelial, and stromal/fibroblast lineages. In addition, pluripotent mesenchymal stem cells capable of differentiating into cells of the osteogenic, chondrogenic, tendonogenic, adipogenic and myogenic lineages have been shown to reside within the bone marrow microenvironment (Majumdar et al, 1998). There is recent literature indicating that circulating endothelial progenitor/stem cells exist, and that stromal stem cells in marrow serve as a source for continual renewal of cells in a number of non-hematopoietic tissues. A common embryological precursor that gives rise to both hematopoietic and endothelial cells has recently been identified (Suda et al, 1997; Choi et al, 1998; Caprioli et al, 1998).

Recent evidence has also shown that embryonic stem (ES) cells can give rise to endothelial cells (Hirashima et al, 1999).

Fibroblast growth factors (FGFs) can synergize with other factors to stimulate hematopoietic progenitor cell proliferation (Wilson et al, 1991; Quito et al, 1996; Allouche, 1995; Yuen et al, 1998, U.S. Pat. No. 5,612,211; U.S. Pat. No. 5,817,773). It has also been shown that basic FGF (FGF-2) acts to antagonize cytokines that induce differentiation (Burger et al, 1994). In addition, low amounts of FGF-2, on the order of 10–100 pg/ml, induce a more primitive phenotype in human K562 leukemic cells.

It would be very useful to be able to isolate stem cells which are progenitors of endothelial and/or stromal cells. The more primitive the stem cell, the more useful it is in bone marrow transplantation. Furthermore, endothelial stem cells and stromal stem cells, or a stem cell which is a progenitor of both, would find many utilities in repairing damaged vasculature and in treating other conditions where endothelial or stromal cells need to be replenished.

SUMMARY OF THE INVENTION

It is an object of the present invention to overcome the deficiencies in the prior art.

It is another object of the present invention to isolate a new phenotype of stem cells.

It is a further object of the present invention to identify and isolate stem cells for use in stem cell transplantation.

It is yet another object of the present invention to identify and isolate endothelial and/or stromal stem cells.

A small population of cells having a "primitive phenotype", such as $CD34^+$ or $CD34^-lin^-$, has been isolated which express cell surface receptors for fibroblast growth factor (FGF). The population of cells bearing FGF receptors (FGFR) are designated as $FGFR^+$. The $FGFR^+$ primitive phenotype cell population has several unique properties:

(1) The $CD34^+FGFR^+$ cells are predominantly present in the region of the fluorescence-activated cell sorter profile having low forward scatter (FSC) and low side scatter (SSC). Thus, the majority of the cells of the population are very small and of low granularity. These small cells are located in the FSC/SSC region of the fluorescence-activated cell sorter profile that is normally not analyzed, as this area contains many of the dead and apoptotic cells. Interestingly, this region has recently been shown to be the site of a mesenchymal stem cell population (Zohar et al, 1997). The $CD34^-lin^-FGFR^+$ cells have FSC/SSC properties that are similar to those of the $CD34^+FGFR^+$ cells. This $CD34^-lin^-FGFR^+$ population also includes significant numbers of cells with higher FSC properties.

(2) The $CD34^+FGFR^+$ cells are deeply dormant, which is characteristic of a stem cell population. They do not proliferate in culture until 30–60 days after isolation.

The $FGFR^+$ primitive phenotype cell population is a unique stem cell population that is a precursor cell for endothelium and/or hematopoiesis and/or stroma. The $FGFR^+$ primitive phenotype cell population, obtained either from general circulation, the bone marrow, cord blood or embryonic cells, is capable of forming endothelial, blood and stromal cells, depending on the need at the time.

BRIEF DESCRIPTION OF THE DRAWINGS

FIG. 2A is a dot plot of FSC versus SSC of all events with region R1 drawn to eliminate the area containing most of the cell debris and doublets. FIG. 2B is a histogram showing the intensity of staining with the dye 7-aminoactinomycin D (7-AAD). The region R2 is drawn to delineate live cells. FIG. 2C is a dot plot of SSC versus CD34 gated on R1 AND R2. The region R3 is drawn to delineate $CD34^+$ cells. FIG. 2D is a dot plot of FSC versus SSC gated on R1 AND R2 AND R3, thus showing the FSC/SSC characteristics of live $CD34^+$ cells in R1. FIG. 2E is a dot plot of CD34 versus FGFR gated on R1 AND R2. The region R4 is drawn to delineate $CD34^+FGFR^+$. FIG. 2F is a dot plot of FSC versus SSC gated on R1 AND R2 AND R4, thereby showing the characteristics of live $CD34^+FGFR^+$ cells in R1.

FIG. 4 is a bar graph showing the growth of various cell populations in the presence or absence of FGF-2 or a combination of FGF-2 plus VEGF.

DETAILED DESCRIPTION OF THE INVENTION

Figure 1:
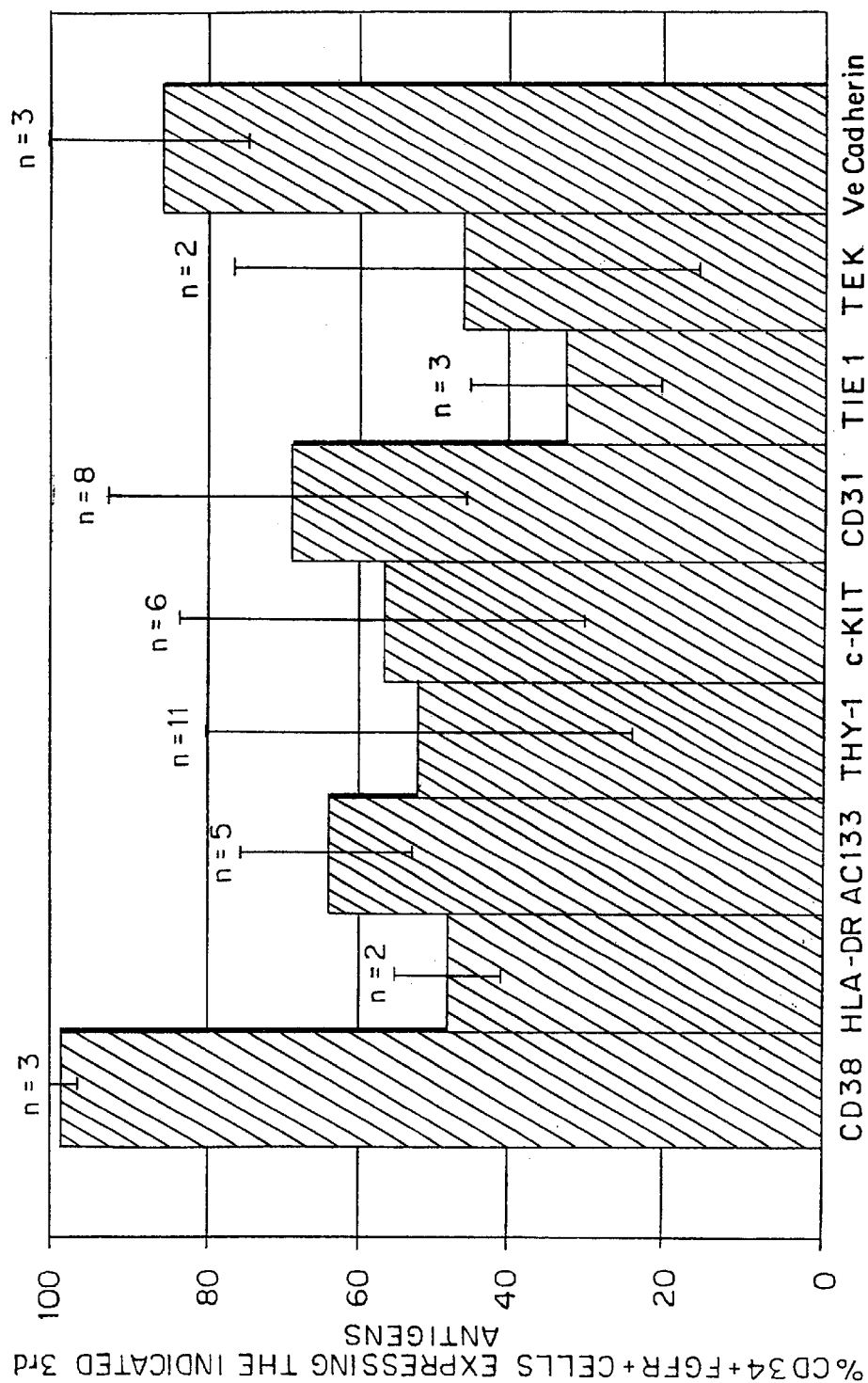
FIG. 1 is a bar graph summarizing the fourteen experiments of Example 1 and showing the percent of $CD34^+FGFR^+$ cells which express the indicated third antigens.

Stem cells, when transplanted, can restore the production of hematopoietic, endothelial and stromal cells to a patient who has lost such production due to, for example, radiation therapy. By isolating $FGFR^+$ primitive phenotype cells, preferably $CD34^+FGFR^+$ or $CD34^-lin^-FGFR^+$, from other cells in the body, it is possible to obtain relatively pure stem cells, preferably separate from contaminating cells and other substances, so that the stem cells can be safely transplanted into a patient in need thereof.

The unique isolated cells of the present invention are separated from other cells by virtue of their $CD34^+$ or $CD34^-lin^-$ state and possession of fibroblast growth factor receptors. The cells can be isolated by conventional techniques for separating cells, such as those described in Civin, U.S. Pat. Nos. 4,714,680, 4,965,204, 5,035,994, and 5,130,144, Tsukamoto et al U.S. Pat. No. 5,750,397, and Loken et al, U.S. Pat. No. 5,137,809, all of which are hereby incorporated by reference in their entirety. Thus, for example, a CD34-specific monoclonal antibody or an FGFR-specific antibody can be immobilized, such as on a column or on magnetic beads. The entire cell population may then be passed through the column or added to the magnetic beads. Those which remain attached to the column or are attached to the magnetic beads, which may then be separated magnetically, are those cells which contain a marker which is recognized by the antibody used. Thus, if the anti-CD34 antibody is used, then the resulting population will be greatly enriched in $CD34^+$ cells. If the antibody used is FGFR, then the resulting population will be greatly enriched in $FGFR^+$ cells. That population may then be enriched in the other marker by repeating the steps using a solid phase having attached thereto an antibody to the other marker.

Another way to sort $CD34^+FGFR^+$ cells is by means of flow cytometry, most preferably by means of a fluorescence-activated cell sorter (FACS), such as those manufactured by Becton-Dickinson under the names FACScan or FACSCalibur. By means of this technique, the cells having a CD34 marker thereon are tagged with a particular fluorescent dye by means of an anti-CD34 antibody which has been conjugated to such a dye. Similarly, the FGFR marker of the cells are tagged with a different fluorescent dye by means of an anti-FGFR antibody which is conjugated to the other dye. When the stained cells are placed on the instrument, a stream of cells is directed through an argon laser beam that excites the fluorochrome to emit light. This emitted light is detected by a photo-multiplier tube (PMT) specific for the emission wavelength of the fluorochome by virtue of a set of optical filters. The signal detected by the PMT is amplified in its own channel and displayed by a computer in a variety of different forms-e.g., a histogram, dot display, or contour display. Thus, fluorescent cells which emit at one wavelength, express a molecule that is reactive with the specific fluorochrome-labeled reagent, whereas non-fluorescent cells or fluorescent cells which emit at a different wavelength do not express this molecule but may express the molecule which is reactive with the fluorochrome-labeled reagent which fluoresces at the other wavelength. The flow cytometer is also semi-quantitative in that it displays the amount of fluorescence (fluorescence intensity) expressed by the cell. This correlates, in a relative sense, to the number of the molecules expressed by the cell.

Flow cytometers are also equipped to measure non-fluorescent parameters, such as cell volume or light scattered by the cell as it passes through the laser beam. Cell volume is usually a direct measurement. The light scatter PMTs detect light scattered by the cell either in a forward angle (forward scatter; FSC) or at a right angle (side scatter; SSC). FSC is usually an index of size, whereas SSC is an index of cellular complexity, although both parameters can be influenced by other factors.

Preferably, the flow cytometer is equipped with more than one PMT emission detector. The additional PMTs may detect other emission wavelengths, allowing simultaneous detection of more than one fluorochrome, each in individual separate channels. Computers allow the analysis of each channel or the correlation of each parameter with another. Fluorochromes which are typically used with FACS machines include fluorescein isothiocyanate (FITC), which has an emission peak at 525 nm (green), R-phycoerythrin (PE), which has an emission peak at 575 nm (orange-red), propidium iodide (PI), which has an emission peak at 620 nm (red), 7-aminoactinomycin D (7-AAD), which has an emission peak at 660 nm (red), R-phycoerythrin Cy5 (RPE-Cy5), which has an emission peak at 670 nm (red), and allophycocyanin (APC), which has an emission peak at 655–750 nm (deep red).

These and other types of FACS machines may have the additional capability to physically separate the various fractions by deflecting the cells of different properties into different containers.

Any other method for isolating the CD34$^+$FGFR$^+$ population of a starting material, such as bone marrow, peripheral blood or cord blood, may also be used in accordance with the present invention. The various subpopulations of the present invention may be isolated in similar manners.

The isolated cell population of this invention can be used in therapeutic methods, such as stem cell transplantation, as well as other therapeutic methods as described below, as well as others that are readily apparent to those skilled in the art. For example, the isolated cell populations can be administered directly by intravenous route to a mammalian patient requiring a bone marrow transplant in an amount sufficient to reconstitute the patient's hematopoietic and immune system. Precise, effective quantities can be readily determined by those skilled in the art and will depend, of course, upon the exact condition being treated by the therapy. In many applications, however, an amount containing approximately the same number of stem cells found in one-half to one liter of aspirated marrow should be adequate.

Thus, a suspension of human cells from marrow or blood comprising cells which are positive both for CD34 and for fibroblast growth factor receptors, preferably substantially free of cells that are not positive for both CD34 and fibroblast growth factor receptors, can restore the production of hematopoietic cells to a human lacking production of these cells. A suspension of these isolated cells is administered to a patient in need thereof in an effective amount to restore production of hematopoietic/endothelial/stromal cells.

The patients in need of this product are those with a specific requirement for hematopoietic, endothelial or stromal cells. For example, patients with vascular injury, persons with genetic defects in their hematopoietic, stromal or endothelial cells, such as collagen deficiency, adenosine deaminase deficiency, or clotting factor deficiency. It is expected that the circulating stem cells will selectively home to sites of hematopoietic, endothelial or stromal cell damage/deficiency.

Other "primitive" phenotype indicators besides CD34$^+$ are also known. These include AC133$^+$ (Buhring et al, 1994; Yin et al, 1997), Thy-1 (Murray et al, 1995) and c-kit$^+$ (Buhring et al, 1994; D'Arena et al, 1998). Another population of primitive cells is CD34$^-$lin$^-$. The present inventors have discovered that the CD34$^+$FGFR$^+$ population of the preferred embodiment of the present invention contains significant amounts of the AC133 marker (approximately 64%), the Thy-1 marker (approximately 52%) or the c-kit marker (approximately 57%). Many of these cells have more than one primitive marker.

Furthermore, certain markers are known to be endothelial markers. These include VE-Cadherin (also known as CD144) (Vittet et al, 1996), TIE-1 (also known as TIE) (Suda et al, 1997), TEK (also known as TIE-2) (Suda et al, 1997; Hamaguchi et al, 1999) and CD31 (also known as PECAM) (Watt et al, 1993). Significant quantities of each of these markers were also found on the CD34$^+$FGFR$^+$ population. About 86% of this population co-expresses VE-Cadherin, about 70% co-expresses CD31; about 47% co-expresses TEK; and about 33% co-expresses TIE-1. This data indicates that the CD34$^+$FGFR$^+$ population includes a primitive population of cells which are precursors of endothelial cells. The subpopulation with these endothelial markers can be isolated and are also part of the present invention. Certain additional markers are known to be stromal cell markers, such as STRO-1 (Gronthos et al, 1994). A subpopulation of the CD34$^+$FGFR$^+$ cells of the present invention which is also STRO-1$^+$ is a primitive population of cells which are precursors of stromal cells. The subpopulation with these stromal markers can be isolated and are also part of the present invention.

The results as to co-expression of additional markers were obtained from fluorescence-activated cell sorter (FACS) analysis using specific antibodies to cell surface antigens. The antibodies were labeled with three or four different fluorochromes. The results show that 100% of live $FGFR^+$ $Thy-1^+$ cells co-express VE-Cadherin, 97% of live $FGFR^+$ $AC133^+$ cells co-express VE-Cadherin, 91% of live $FGFR^+$ $AC133^+$ cells co-express Thy-1, and 67% of live $FGFR^+$ $TEK^+$ cells co-express Thy-1. Cell sorter systems using additional fluorochromes will be able to allow the separation of those cells in the $CD34^+FGFR^+$ population which also express two or more of the various other primitive or endothelial markers discussed above. Similarly, other markers, such as the vascular endothelial growth factor-receptor (VEGF-R) (also known as KDR), which is a marker for endothelial cells, can also be included in such analyses. It is predicted that a subpopulation of $CD34^+FGFR^{+Thy-1+}$ $VEGF-R^+$ cells exist, which subpopulation can be identified and isolated by such systems by one of ordinary skill in the art without undue experimentation. This subpopulation represents a progenitor population capable of developing into either or both of the hematopoietic and endothelial lineages.

The isolated $CD34^+FGFR^+$ cells grow exceedingly slowly in culture with a long lag of 4–6 weeks. The cells grow in an FGF-dependent manner, as shown in Example 3 and Table 5. A long dormant period is associated with a stem cell phenotype, indicating that these cells have growth characteristics compatible with stem cells.

While the $CD34^+FGFR^+$ cells can be isolated in substantial purity, i.e., in a substantially homogeneous population, by the methods discussed above, such as, for example, by means of the FACS apparatus, it is not always necessary that the $CD34^+FGFR^+$ stem cell population of the present invention be present in substantial purity. For example, for most purposes, it is sufficient if the population of cells contains greater than 90% of human stem cells characterized as $CD34^+$ and $FGFR^+$ or $FGFR^+$ with another indication of primitive phenotype. Other aspects of the present invention include subpopulations of the $FGFR^+$ primitive phenotype population which are substantially homogeneous for other markers. This includes the subpopulation of the $FGFR^+$ primitive phenotype human stem cells which are also positive for any one or more of the endothelial markers, any one or more additional primitive markers and/or any one or more of stromal cell markers, which subpopulation is substantially homogeneous or is a composition wherein greater than 90% of said cells are $FGFR^+$ primitive phenotype and positive for one or more of those additional markers. Thus, the subpopulation may be a substantially homogeneous population or a composition in which greater than 90% of the cells therein are $CD34^+FGFR^+$ (or $CD34^-lin^-FGFR^+$) and $TIE-1^+$. The subpopulation may also be a substantially homogeneous population or a composition in which greater than 90% of the cells therein are $CD34^+FGFR^+$ (or $CD34^-lin^-FGFR^+$) and $CD31^+$ and/or $TEK^+$ and/or $VEGFR^+$ and/or $VE-Cadherin^+$ and/or positive for any other endothelial marker. Similarly, the subpopulation may be a substantially homogeneous population or a composition in which greater than 90% of the cells therein are $CD34^+FGFR^+$ (or $CD34^-lin^-FGFR^+$) and positive for one or more of the other primitive markers, such as AC133, Thy-1 and c-kit. The subpopulation may also be a substantially homogeneous population or a composition in which greater than 90% of the cells therein are $CD34^+FGFR^+$ (or $CD34^-lin^-FGFR^+$) and also positive for one or more of the other primitive markers and further positive for one or more of the endothelial markers. The subpopulation may also be a substantially homogeneous population or a composition in which greater than 90% of the cells therein are $CD34^+FGFR^+$ (or $CD34^-lin^-FGFR^+$) and also positive for one or more of stromal markers, such as $CD34^+FGFR^+$ (or $CD34^-lin^-FGFR^+$) and $STRO-1^+$. Such subpopulations are also contemplated by the present invention.

With some of the utilities of the present invention, such as, for example, bone marrow transplantation, the stem cell population may be a substantially smaller percent of the total cell count being administered. The remaining cells may be filler cells, which may be cells incapable of replicating. Alternatively, the remaining cells may be any of the other types of cells from which the cells of the present invention are originally separated. Thus, for example, the present invention also comprehends populations containing at least 20% of any of the phenotypes of the present invention, i.e., $CD34^+FGFR^+$, $CD34^-lin^-FGFR^+$, $CD34^+FGFR^+Thy-1^+$, $CD34^+FGFR^+TIE-1^+$, $CD34^+FGFR^+CD31^+$, $CD34^+FGFR^+$ $VEGF-R^+$, $CD34^+FGFR^+Thy-1^+VEGF-R^+$, etc. Such a low purity subpopulation still defines over the prior art and yet maintains many of the advantages of the present invention for many of its proposed utilities. Compositions having greater than 30%, 40%, 50%, 60%, 70% or 80% of cells of any of the phenotypes of the present inventions are also considered to be part of the present invention.

Another way of defining the cellular compositions of the present invention is as a suspension of human cells, comprising pluripotent stem cells or endothelial stem cells which are substantially free of mature lymphoid and myeloid cells. Cells substantially all of which are of the $FGFR^+$ primitive phenotype are substantially free of mature lymphoid and myeloid cells.

Although the present invention has thus far been primarily described with respect to the preferred embodiment of $CD34^+FGFR^+$ cells, it should be understood that $FGFR^+$ cells having other indications of primitive phenotype are also contemplated in accordance with the present invention. For example, $CD34^-$ cells which are also negative for lineage markers ($lin^-$) may be even more primitive than $CD34^+$ cells (see Zanjani et al, 1999). Thus, the $CD34^-lin^-$ phenotype is also considered to be an indication of primitiveness in accordance with the present invention. Additionally, when embryonic stem cells are used as the source of cells from which the population of the present invention is to be separated, all such cells, by definition, have a primitive phenotype. Thus, $FGFR^+$ cells separated from an embryonic stem cell source will inherently be $FGFR^+$ cells with a primitive phenotype. Furthermore, other primitive markers, such as AC133, Thy-1 and c-kit, may also be used as markers for primitiveness. Thus, in its broadest aspect, the present invention relates to phenotypes which are $FGFR^+$, as well as positive for any phenotype indicating primitive state cells, including, but not limited to, $CD34^+$, $CD34^-lin^-$, being embryonic stem cells, $AC133^+$, $Thy-1^+$ and $c-kit^+$. The present invention further relates to subpopulations thereof as described above.

The pluripotent FGFR⁺ primitive phenotype stem cells, or pluripotent stem cells of any of the other phenotypes of the present invention, have considerable commercial use, including one or more of the following:

(1) For bone marrow transplantation.

(2) To target delivery of anti-tumor agents. Endothelial stem cells of the present invention can be used to target the delivery of angiostatic agents and anti-tumor agents to the rapidly proliferating vascular bed associated with tumors. Endothelial cells are long-lived, and the stem cells can be used as vectors to deliver angiostatic/antitumor agents to the rapidly expanding vascular bed associated with tumors without affecting the stable endothelium of established blood vessels.

(3) To coat valves and devices used in surgical procedures. The endothelial stem cells of the present invention can be used to coat valves and implant devices, eliminating many of the clotting problems currently associated with these devices. The endothelial stem cells can be cultured from specific individuals so that valves, implant devices, etc., may be coated with autologous endothelial cells. Panels of HLA-matched endothelial stem cells can also be produced for these purposes.

(4) As vectors for genetic engineering. Genetically engineered stem cells "homing" to the endothelium, bone marrow, or connective tissue stroma are long-lived and can secrete proteins, such as adenosine deaminase or clotting factors, as well as other proteins, such as t-PA, which promote thrombolysis. A wild-type gene can be incorporated into the endothelial stem cells, either by homologous or random recombination. With allogeneic endothelial stem cells, normal cells lacking the genetic defect can be used therapeutically. Other indications for gene therapy are introduction of drug resistance genes to enable normal stem cells to have an advantage and be subject to selective pressure, e.g., the multiple drug resistance gene. Disease other than those associated with endothelial cells may also be treated, where the disease is related to the lack of a particular excreted product, such as a hormone, enzyme, interferon, factor, or the like. By employing an appropriate regulatory initiation region, inducible production of the deficient protein is achieved so that production of the protein parallels natural production, even though production is in a different cell type from the cell type that normally produces such protein. A ribozyme, antisense or other message can be inserted to inhibit particular gene products or susceptibility to disease.

(5) To repair sites of vascular injury. Engineered endothelial stem cells secreting such factors as tissue plasminogen activator, designed to help prevent restenosis after balloon angioplasty, can be infused. Asahara et al (1997) have demonstrated that endothelial stem cells selectively home to sites of vascular damage.

(6) To isolate new molecules that are important in stem and tumor cell biology.

(7) To form endothelium, stroma and blood cells, depending on the need at the time.

The stem cells of the present invention can be expanded in number by long-term in vitro culture with minimal differentiation until needed. However, the stem cells can produce blood cells when treated with the appropriate hematopoietic growth and differentiation factors, or form tubular network structures characteristic of endothelial cells upon treatment with the appropriate agents, or form fibroblast-like stromal cells upon treatment with the appropriate agents. Additionally, the cultured stem cells of the present invention can mature into functionally competent blood cells in vivo, capable of mediating antigen-specific immune responses, repopulating lympho-hematopoietic organs, and prolonging survival of animals with a destroyed hematopoietic system.

Although the phenotype of the particular stem cells isolated according to the present invention is new, one skilled in the art could readily, without undue experimentation, be able to use the stem cells of the present invention in the capacities described above, as well as in other capacities. Illustrations of such use are found in Wagner et al, U.S. Pat. No. 5,744,347.

The following materials and methods are applicable to all of the following examples.

Materials and Methods

Source of Human Cells

Fresh or frozen cells from bone marrow, cytokine mobilized peripheral blood or cord blood were obtained from donors after informed consent.

Bone marrow or cord blood samples were diluted with 4 volumes RPMI 1640 medium containing 10% fetal calf serum (FCS). Mononuclear cells were separated on a Histopaque®-1077 density gradient (Sigma Diagnostics, St. Louis, Mo.) and washed×2 with PBS-citrate (PBS containing 13.6 mmol/L sodium citrate, 1 mmol/L adenosine and 2 mmol/L theophylline).

Leukapheresis samples were not normally subjected to Histopaque®-1077 density gradient centrifugation but were washed ×2 with PBS-citrate before proceeding to the filtration step.

PBS-citrate washed cells (from all sources) were filtered through a 40 μm nylon cell strainer (Falcon 2340, Becton-Dickinson, N.J.). Cells were resuspended in 2 ml PBS-citrate and overlaid on a 3 ml PBS-citrate/10% bovine serum albumin (BSA) cushion and then centrifuged for 10 minutes at 200 g at room temperature, to remove platelets (Thoma et al, 1994). This step was repeated once or twice.

If necessary DNase was used to digest DNA from cell debris.

Immunomagnetic Separation

Samples were enriched for CD34⁺ cells by one of the following methods:

(a) magnetic activated cell sorting (MACS) columns, using anti-CD34 antibodies coated onto uniform, supermagnetic, polystyrene beads (Miltenyi Biotec, Auburn, Calif.). Separation was carried out on a Mini-MACS device according to manufacturer's recommendation (Mitenyi Biotec, Auburn, Calif.).

(b) magnetic separation using the Dynal CD34 Progenitor Cell Selection System (Dynal A. S., Oslo, Norway), which also uses anti-CD34 antibodies immobilized onto microbeads. In both techniques magnetically labeled cells are separated from other cells by means of a magnetic field.

Antibodies and Reagents

The following antibodies were used for immunofluorescent staining: CD34-FITC, CD34-PE, CD34-RPE-CY5, c-kit-PE, CD38-FITC, Mouse IgG-FITC, Mouse IgG-PE, Mouse IgG-RPE-Cy5, Mouse IgG2a, streptavidin-PE and goat-anti-mouse-RPE were purchased from Dako (Dako A/S, Glostrup, Denmark). Thy-1-FITC and Thy-1-PE were obtained from Immunotech (Immunotech, France). CD31-FITC, Mouse IgG Biotin, CD34-APC and Mouse IgG APC were obtained from Caltag (Caltag Laboratories, Burlingame, Calif.). HLA-DR-FITC, Mouse IgG and Goat IgG were purchased from Sigma (Sigma®, St. Louis Mo.) and CD34-APC, CD31-PE, Mouse IgG-APC from Becton-Dickinson (Becton-Dickinson, San Jose, Calif.). AC133-PE was obtained from Miltenyi (Miltenyi Biotec, Auburn, Calif.). VE-Cadherin-FITC was a kind gift from Dr. W. A. Muller, Cornell University, New York. TIE 1-FITC, TIE 1-PE, biotinylated TIE 1 and biotinylated TEK were generous gifts from Dr. T. Suda, Kumamoto University, Kumamoto, Japan. FGF-R1 antibody was obtained from Dr. W. L. McKeehan, Texas A and M University, Houston, Tex. or commercially, from QED Bioscience Inc.(San Diego, Calif.). Anti-FGF-R1-FITC was either purchased from QED or prepared in our laboratory. Anti-FGF-R1-APC was produced, purified and conjugated to allophycocyanin (APC) in our own laboratory. Conjugation of the antibody to APC was performed using a PhycolinkT conjugation kit, PJ25C, purchased from Prozyme (Prozyme, San Leandro, Calif.).

Cell Staining and Flow Cytometry

MACS-selected or Dynal-selected CD34$^+$ cells were resuspended in PBS/0.1% BSA/0.01% NaN$_3$/Aprotinin 20 µg/ml (PBS/BSA/N$_3$/Aprotinin). Fc receptors and non specific binding of immunoglobulins to cell surfaces were blocked with human IgG and either mouse or goat IgG where appropriate. Cells were incubated with appropriate antibodies for 30 minutes on ice. After washing ×2 with PBS/BSA/N$_3$/Aprotinin, cells were analyzed on a FACS-Calibur flow cytometer (Becton-Dickinson, San Jose, Calif.), equipped with an argon laser to excite FITC, PE and RPE-CY5 fluorochromes and a helium-neon diode, with time delay adjusted according to manufacturer's recommendations, for excitation of allophycocyanine (APC). 30,000 to 150,000 CD34$^+$ selected cells were analyzed using CellQuest software (Becton-Dickinson, San Jose, Calif.). The dye, 7-aminoactinomycin D (7-AAD) (Sigma, St. Louis, Mo.), was used in some experiments to identify dead cells. This was done to ensure that the CD34$^+$FGFR$^+$ population was a viable population.

Cell Sorting

To isolate and study the growth characteristics of the CD34$^+$FGFR$^+$ population, CD34$^+$ selected cells were obtained as previously described. These cells were incubated with antibodies to CD34 and FGF-R1 (as described above) and sorted on a Coulter Epics Elite (Beckman Coulter Inc., Fullerton, Calif.) into CD34$^+$FGFR$^+$ and CD34$^+$ FGFR$^-$ populations. Sorted cells were incubated in a variety of media, including RPMI 1640, αMEM, DMEM and long term culture medium (LTCM) (Myelocult H5100 from StemCell Technologies Inc., Vancouver, Canada) containing 12.5% horse serum and 12.5% FCS in the presence or absence of growth factors such as FGF-2 and VEGF. Growth was assessed by determining the number of cells present at various time points.

EXAMPLE 1

CD34$^+$FGFR$^+$ Co-Expression of Other Antigens

CD34-enriched cells were purified from cytokine mobilized peripheral blood (PB), bone marrow (BM), or cord blood (CB), using magnetic separation techniques (Dynal or MiniMacs). Fluorescent-labeled antibodies were used to assay for CD34$^+$FGFR$^+$ cells and a percentage of CD34$^+$ FGFR$^+$ was determined for each experiment. The results of the fourteen experiments which were run are shown in Table 1. For the fourteen experiments, a mean of 4.4% (±2.3%) of CD34$^+$ cells expressed FGFR.

The presence of a third antigen on the CD34$^+$FGFR$^+$ cells was also ascertained using fluorescent antibodies. The mean percentage of CD34$^+$FGFR$^+$ cells expressing a particular third antigen is shown in Table 1 and is shown graphically in FIG. 1. The error bars indicate the standard deviation (SD) and the numbers show the number of experiments assaying a particular antigen.

The experiments were run by submitting the CD34$^+$ or CD34$^-$lin$^-$ enriched cells to the Becton-Dickinson FACS-Calibur machine using the CellQuest System software for three- and four-color analysis. The techniques were similar to those described in "Flow Cytometry Analysis Using the Becton-Dickinson FACScan", *Current Protocols in Immunology*, unit 5.4, pages 5.4.1–5.4.19 (Supplement 16, 1995).

TABLE 1

| Experiment # | Source | Selecton Method | % CD34$^+$FGFR$^+$ | % CD34$^+$FGFR$^+$ Cells Expressing the Indicated Third Antigens | | | | | | | | |
|---|---|---|---|---|---|---|---|---|---|---|---|---|
| | | | | CD38 | HLA-Dr | AC133 | Thy-1 | c-kit | CD31 | Tie 1 | TEK | VE-Cadherin |
| 1 | PB | Dyn | 3.2 | 100 | 43 | | 97 | | | | | |
| 2 | PB | Macs | 7.9 | | | | | | 66 | | | |
| 3 | PB | Macs | 3.6 | | | | 50 | | 38 | | | |
| 4 | PB | Macs | 3.1 | 100 | | | 38 | | 85 | 29 | | |
| 5 | PB | Macs | 3.9 | | | 50 | | | | | | |
| 6 | PB | Macs | 6.6 | | | 67 | 26 | 94 | 99 | 23 | | |
| 7 | PB | Macs | 3.6 | 96 | 53 | 73 | 57 | 40 | 97 | 47 | 25 | 85 |
| 8 | PB | Macs | 8.2 | | | 76 | 87 | | | | 68 | 99 |
| 9 | BM | Dyn | 4.9 | | | | 94 | 78 | 52 | | | |
| 10 | BM | Macs | 2.1 | | | | 29 | 28 | 74 | | | |
| 11 | CB | Dyn | 5.8 | | | | | | | | | |

TABLE 1-continued

| Experiment # | Source | Selecton Method | % CD34+FGFR+ | % CD34+FGFR+ Cells Expressing the Indicated Third Antigens | | | | | | | | |
|---|---|---|---|---|---|---|---|---|---|---|---|---|
| | | | | CD38 | HLA-Dr | AC133 | Thy-1 | c-kit | CD31 | Tie 1 | TEK | VE-Cadherin |
| 12 | CB | Macs | 1.3 | | | | | | | | | |
| 13 | CB | Macs | 6.5 | | | | 31 | | | | | |
| 14 | CB | Macs | 1.1 | | | 55 | 23 | 67 | | | | |
| | | Mean | 4.4 | 99 | 48 | 64 | 52 | 57 | 70 | 33 | 47 | 66 |
| | | SD | 2.3 | 2 | 7 | 11 | 28 | 27 | 23 | 12 | 30 | 12 |
| | | n | 14 | 3 | 2 | 5 | 11 | 6 | 7 | 3 | 2 | 3 |

SD = Standard Deviation
n = Number
99% of CD34+FGFR+ cells CO-express CD38 (range 96%–100%)
86% of CD34+FGFR+ cells co-express VE-Cadherin (range 75%–99%)
70% of CD34+FGFR+ cells co-express CD31 (range 38%–99%)
64% of CD34+FGFR+ cells co-express AC133 (range 50%–76%)
57% of CD34+FGFR+ cells co-express c-kit (range 28%–94%)
52% of CD34+FGFR+ cells co-express Thy-1 (range 23%–97%)
48% of CD34+FGFR+ cells co-express HLA-Dr (range 43%–68%)
47% of CD34+FGFR+ cells co-express TEK (range 25%–68%)
33% of CD34+FGFR+ cells co-express Tie-1 (range 23%–47%)

Figure 2A:
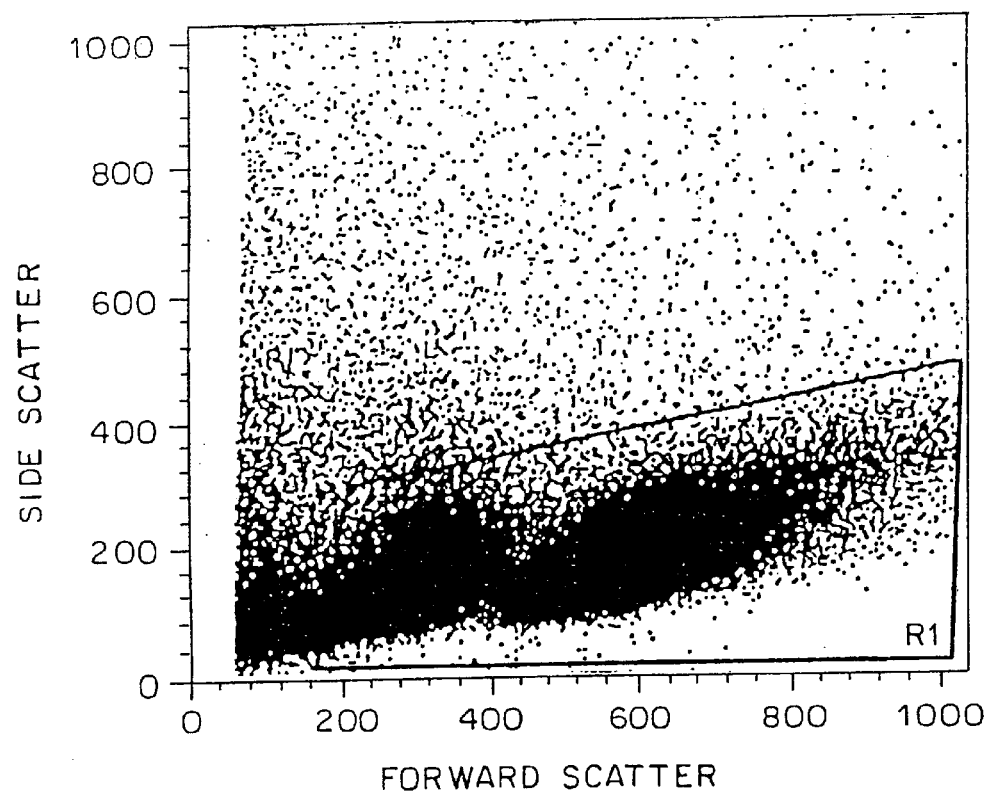
FIGS. 2A–2F are flow cytometry plots for Experiment 7 of Example 1.

It can be seen that in Experiment 7 results were obtained for third antigens from each of the panel of nine different antigens. The results of Experiment 7 are tabulated in Table 2. Furthermore, flow cytometry plots for Experiment 7 are shown in FIGS. 2A–2F. FIG. 2A is a dot plot of forward scatter (FSC) versus side scatter (SSC) of all events. FSC gives an indication of cell size, i.e., low FSC equals small size. SSC gives an indication of cell granularity or complexity, i.e., low SSC equals low granularity. A region R1 is drawn to delineate cells of low-to-high FSC and low-to-medium SSC. This eliminates the area containing most of the cell debris and doublets.

Figure 2B:
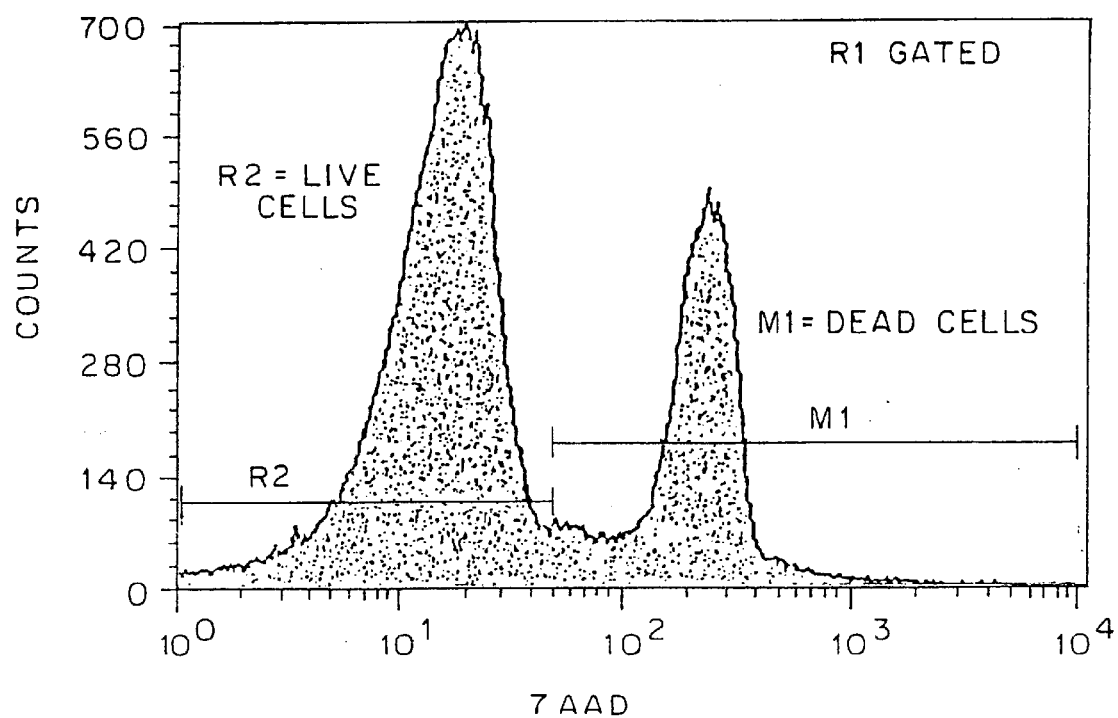

FIG. 2B is a histogram showing the intensity of staining with the dye 7-AAD (Philpott et al, 1996). 7-AAD is a large molecule which is not readily taken up by cells with intact cell membranes and which stains dead cells intensely. The histogram is gated on R1, and the region R2 is drawn to delineate live cells.

Figure 2C:
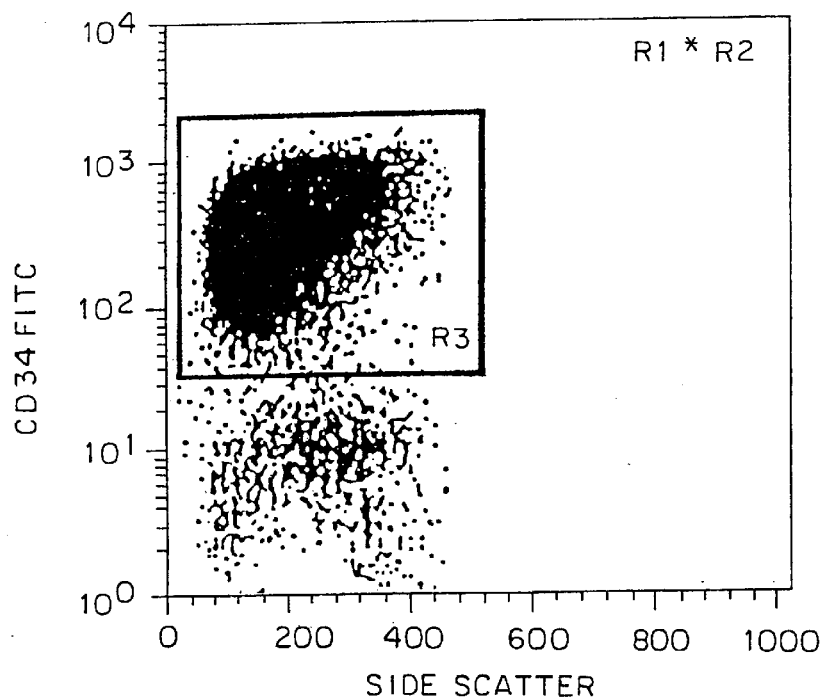

FIG. 2C is a dot plot of SSC versus CD34 gated on R1 AND R2. The gates are set using Boolean logic in which the convention used for R1 AND R2 is R1*R2, and in this instance the gate delineates live cells in R1. The region R3 is drawn to delineate CD34+ cells in this plot. FITC was used to label the CD34+ cells.

Figure 2D:
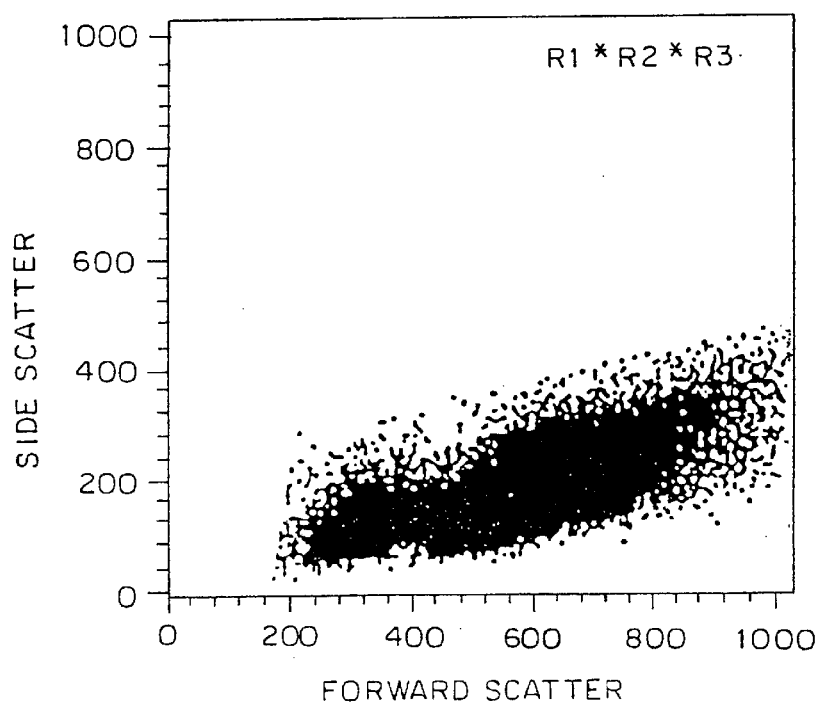

FIG. 2D is a dot plot of FSC versus SSC gated on R1 AND R2 AND R3 (R1*R2*R3), i.e., this plot uses "backgating" to show the FSC/SSC characteristics of live CD34+ cells in R1.

Figure 2E:
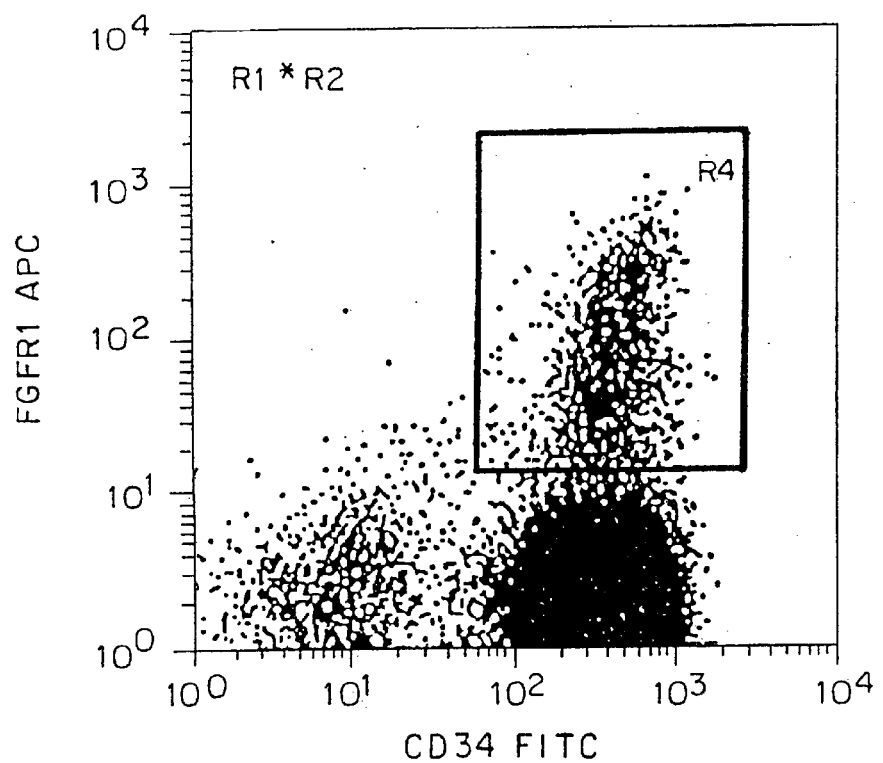

FIG. 2E is a dot plot of CD34 versus FGFR gated on R1 AND R2, i.e., gated on live cells in R1. The region R4 is drawn to delineate CD34+FGFR+ cells.

Figure 2F:
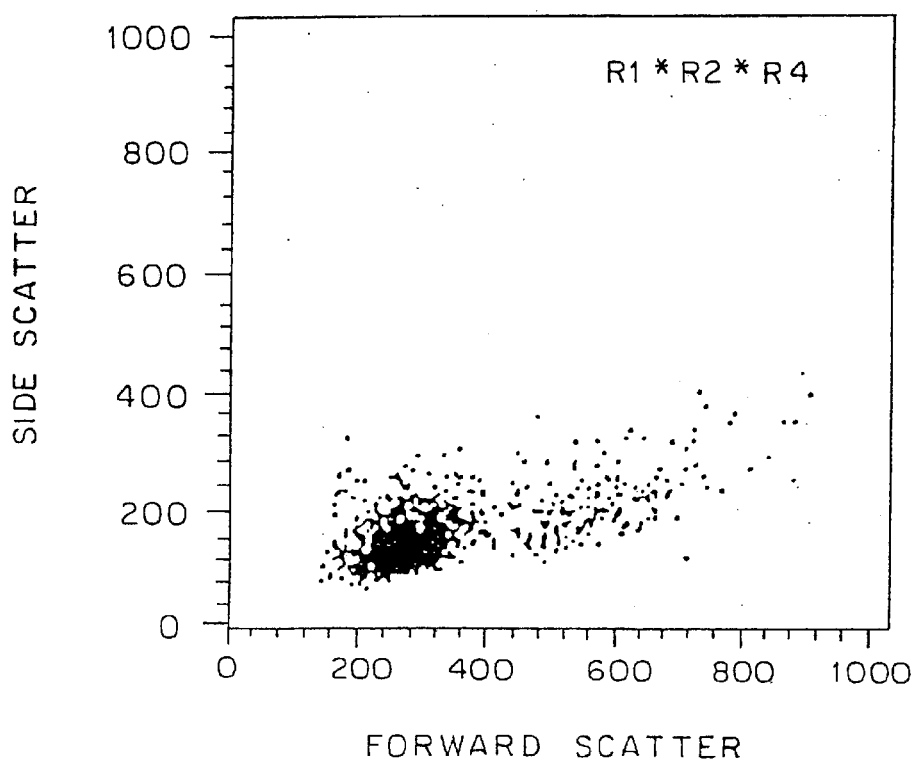

FIG. 2F is a dot plot of FSC versus SSC gated on R1 AND R2 AND R4 (R1*R2*R4), i.e., this plot uses "backgating" to show the characteristics of live CD34+FGFR+ cells in R1. It is noted that the majority of live CD34+FGFR+ cells have low FSC and low SSC, i.e., they are small cells with low granularity. The position of these cells on the scatter dot plot is somewhat unusual, as it appears in the region which is conventionally ignored.

TABLE 2

Experiment 7: Analysis of Live CD34+FGFR+ Population from Cytokine Mobilized Peripheral Blood

| Number of CD34+ Cells | Number of CD34+FGFR+ Cells | % CD34+FGFR+ (% of CD34+) | Phenotype | Number of Cells of Each Phenotype | Phenotype (% of CD34+ Population) | Phenotype (% of CD34+FGFR+ Population) |
|---|---|---|---|---|---|---|
| 90121 | 4039 | 4.48 | CD34+FGFR+CD38+ | 3876 | 4.30 | 96 |
| 104819 | 4829 | 4.61 | CD34+FGFR+HLA-DR+ | 2561 | 2.44 | 53 |
| 90803 | 2910 | 3.20 | CD34+FGFR+AC133+ | 2106 | 2.32 | 73 |
| 111007 | 4773 | 4.30 | CD34+FGFR+c-kit+ | 1923 | 1.73 | 40 |
| 100291 | 2805 | 2.80 | CD34+FGFR+THY-1+ | 1594 | 1.59 | 57 |
| 86441 | 2957 | 3.42 | CD34+FGFR+CD31+ | 2869 | 3.32 | 97 |
| 8478 | 2956 | 3.50 | CD34+FGFR+VE-Cadherin+ | 2524 | 2.99 | 85 |
| 100148 | 3969 | 3.96 | CD34+FGFR+TIE+ | 1866 | 1.86 | 47 |
| 100758 | 2491 | 2.47 | CD34+FGFR+TEK+ | 686 | 0.68 | 28 |

Mean: 3.64
SD 0.75
Mean % CD34+ cells per sample = 98% (±0.65)

Figure 3:
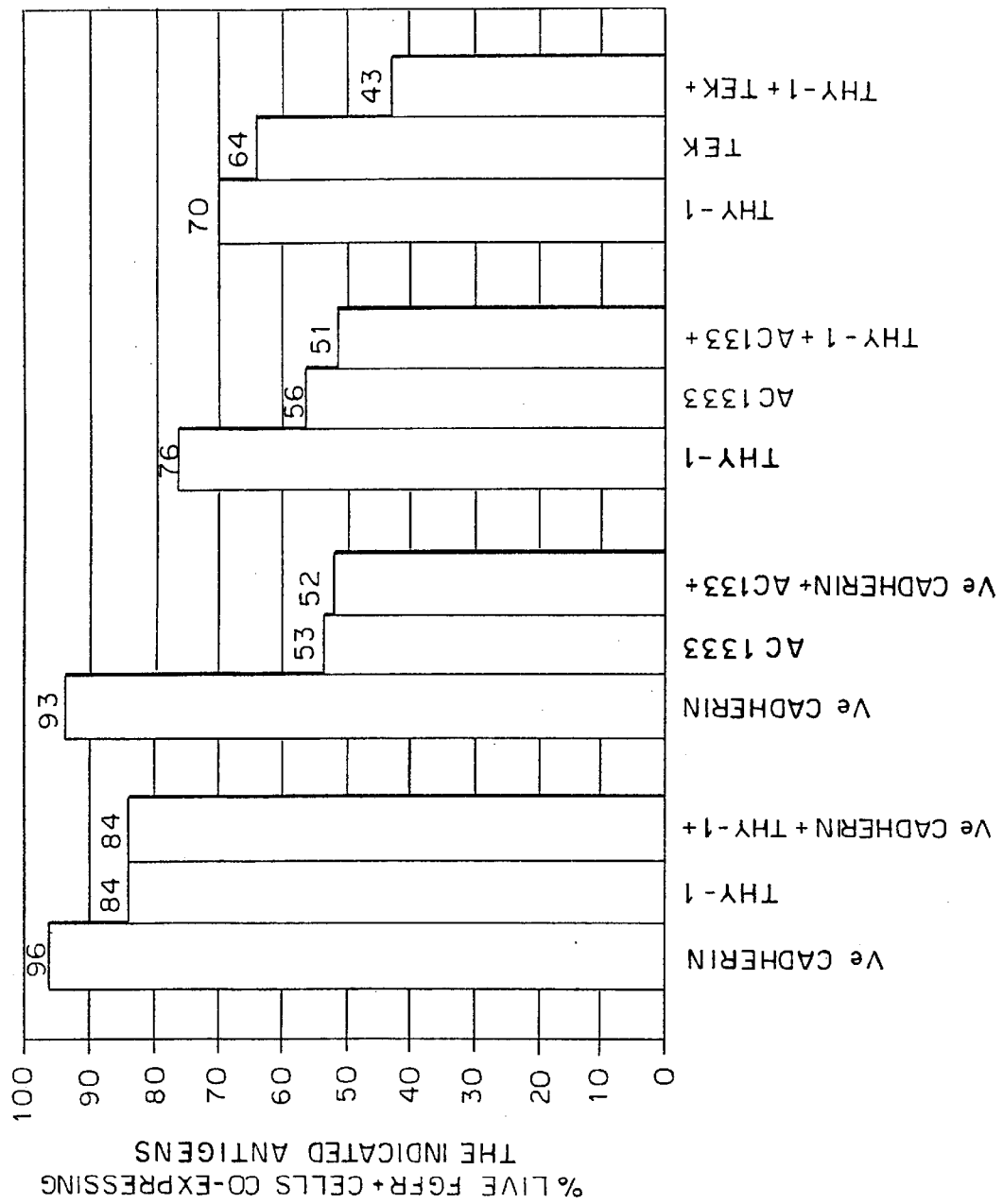
FIG. 3 is a bar graph showing the percent of live $FGFR^+$ cells co-expressing the indicated antigens.

Table 3 shows the results of some of the samples from Experiment 8. In these samples, CD34 staining was not included in order that other combinations of antigens could be assayed. FIG. 3 shows these results graphically. One can see that all live FGFR$^+$Thy-1$^+$ cells co-express VE-Cadherin as do 97% of live FGFR$^{+AC}$133$^+$ cells. Since 99% of CD34$^+$FGFR$^+$ cells in Experiment 8 were found to be VE-Cadherin$^+$, one can extrapolate from this experiment that the phenotype of the CD34$^+$FGFR$^+$ population is CD34$^+$FGFR$^+$VE-Cadherin$^+$Thy-1$^{+AC}$133$^+$ and that approximately two-thirds are TEK$^+$.

stained with fluorescent-labeled antibodies to CD34 and FGFR and sorted on a fluorescence-activated cell sorter (FACS) into FGFR$^+$ and FGFR$^-$ populations. Cells were seeded at 1000 cells per well into collagen/gelatin coated wells containing long-term culture medium (LTCM) with either (a) no additions, (b) 10 ng/ml FGF-2 or (c) 10 ng/ml FGF-2 plus 10 ng/ml VEGF, and incubated at 37° C. in a

TABLE 3

Experiment 8: Analysis of Live FGFR$^+$ Cells from Cytokine Mobilized Peripheral Blood

| Sample # | Number of LIVE FGFR$^+$ Cells | | Number of Cells of Each Phenotype | % of LIVE FGFR$^+$ Population | |
|---|---|---|---|---|---|
| 1 | 635 | LIVE FGFR$^+$VE-CADHERIN$^+$ | 609 | 96 | |
|  |  | LIVE FGFR$^+$THY-1$^+$ | 534 | 84 | 1a |
|  |  | LIVE FGFR$^+$VE-CADHERIN$^+$THY-1$^+$ | 535 | 84 | 1b |
| 2 | 594 | LIVE FGFR$^+$VE-CADHERIN$^+$ | 550 | 93 | |
|  |  | LIVE FGFR$^+$AC133$^+$ | 316 | 53 | 2a |
|  |  | LIVE FGFR$^+$VE-CADHERIN$^+$AC133$^+$ | 307 | 52 | 2b |
| 3 | 356 | LIVE FGFR$^+$THY-1$^+$ | 270 | 76 | |
|  |  | LIVE FGFR$^+$AC133$^+$ | 198 | 56 | 3a |
|  |  | LIVE FGFR$^+$THY$^+$AC133$^+$ | 181 | 51 | 3b |
| 4 | 627 | LIVE FGFR$^+$THY-1$^+$ | 441 | 70 | |
|  |  | LIVE FGFR$^+$TEK$^+$ | 399 | 64 | 4a |
|  |  | LIVE FGFR$^+$THY-1$^+$TEK$^+$ | 269 | 43 | 4b |

Table 3 shows that in this experiment:
All live FGFR$^+$THY-1$^+$ cells co-express VE-Cadherin (1a, 1b)
About 97% of live FGFR$^+$AC133$^+$ cells co-express VE-Cadherin (2a, 2b)
At least 91% of live FGFR$^+$AC133$^+$ cells co-express THY-1 (3a, 3b)
At least 67% of live FGFR$^+$TEK$^+$ cells co-express THY-1 (4a, 4b)

EXAMPLE 2

CD34$^-$lin$^-$FGFR$^+$ Co-Expression of Other Antigens

The following experiment was conducted using the techniques described for Example 1. Lineage depletion to obtain lin$^-$ cells was conducted as described in Bhatia et al, 1997, and Bhatia et al, 1998, using Dynal beads and magnetic separation. The results obtained are summarized in Table 4. It can be seen that 77% of CD34$^-$lin$^-$FGFR$^+$ cells co-express CD31, 40% of CD34$^-$lin$^-$FGFR$^+$ cells co-express c-kit, 47% of CD34$^-$lin$^-$FGFR$^+$ cells co-express VE-Cadherin, and 18% of CD34$^-$lin$^-$FGFR$^+$ cells co-express TIE-1.

TABLE 4

| Expt | CD34 | % of CD34$^+$ or CD34-LIN$^-$FGFR$^+$ Cells Expressing Third Antigen | Cell Number |
|---|---|---|---|
| (a) | + | 96% of CD34$^+$LIN$^-$FGFR$^+$ cells are CD31$^+$ | 572 |
|  | − | 77% of CD34$^-$LIN$^-$FGFR$^+$ cells are CD31$^+$ | 211 |
|  | + | 97% of CD34$^+$LIN$^-$FGFR$^+$ cells are c-kit$^+$ | 1500 |
|  | − | 40% of CD34$^-$LIN$^-$FGFR$^+$ cells are c-kit$^+$ | 107 |
| (b) | + | 75% of CD34$^+$LIN$^-$FGFR$^+$ cells are VE-Cadherin$^+$ | 417 |
|  | − | 47% of CD34$^-$LIN$^-$FGFR$^+$ cells are VE-Cadherin$^+$ | 570 |
|  | + | 42% of CD34$^+$LIN$^-$FGFR$^+$ cells are TIE 1$^+$ | 237 |
|  | − | 13% of CD34$^-$LIN$^-$FGFR$^+$ cells are TIE 1$^+$ | 162 |
| (c) | + | 37% of CD34$^+$LIN$^-$FGFR$^+$ cells are TIE 1$^+$ | 1133 |
|  | − | 23% of CD34$^-$LIN$^-$FGFR$^+$ cells are TIE 1$^+$ | 1625 |

EXAMPLE 3

Growth Characteristics

Cytokine mobilized peripheral blood cells were enriched for CD34$^+$ cells using magnetic separation. The cells were humidified incubator. After 4–6 weeks, the number of cells per well were counted. The results are shown in Table 5 and shown graphically in FIG. 4. It can be seen that the FGFR$^+$ population grows in an FGF dependent manner and that the addition of VEGF together with FGF-2 further increases the growth of the cells.

TABLE 5

| | | Cell Growth (cells/well) | | |
|---|---|---|---|---|
| | | | ADDITIONS | |
| Expt | Population | None | FGF-2 (10 ng/ml) | FGF-2 + VEGF (both at 10 ng/ml) |
| (i) | CD34$^+$FGFR$^+$ | 1734 | 11978 | ND |
|  | CD34$^+$FGFR$^-$ | 1244 | 2500 | ND |
| (ii) | CD34$^+$ | 1617 | 1457 | 2311 |
|  | CD34$^+$FGFR$^+$ | 3227 | 8057 | 17140 |
|  | CD34$^+$FGFR$^-$ | 1493 | 2098 | 3093 |

All references cited herein, including journal articles or abstracts, published or unpublished U.S. or foreign patent applications, issued U.S. or foreign patents, or any other references are entirely incorporated by reference herein, including all data, tables, figures and text present in the cited references. Additionally, the entire contents of the references cited within the references cited herein are also incorporated by reference in their entirety.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . ." and "means for . . .", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation.

What is claimed is:

1. A composition comprising a physiologically acceptable medium and human stem cells, wherein greater than 20% of said cells are human stem cells characterized as $FGFR^+$ and also having another indicator of a primitive state, with the proviso that said human stem cells are not embryonic stem cells.

2. A composition in accordance with claim 1, wherein said indicator of a primitive state is selected from the group consisting of $CD34^+$, $CD34^-lin^-$, $Thy-1^+$, $AC133^+$ and $c-kit^+$.

3. A composition in accordance with claim 2, wherein said indicator of a primitive state is $CD34^+$.

4. A composition in accordance with claim 2, wherein said indicator of a primitive state is $CD34^-lin^-$.

5. The composition according to claim 1, wherein said human stem cells are selected from the group consisting of endothelial stem cells, stromal stem cells and hematopoietic stem cells.

6. The composition according to claim 1, wherein greater than 20% of said cells are human stem cells characterized as $FGFR^+$ and either $CD34^+$ or $CD34^-lin^-$ and further having one or more of the markers $Thy-1^+$, $AC133^+$ and $c-kit^+$.

7. The composition according to claim 1, wherein greater than 20% of said cells are human stem cells characterized as $FGFR^+$ and either $CD34^+$ or $CD34^-lin^-$ and further having one or more markers indicative of endothelial cells.

8. A composition in accordance with claim 7, wherein said markers indicative of endothelial cells are selected from the group consisting of $TIE-1^+$, $TEK^+$, $CD31^+$, $VE-Cadherin^+$ and $VEGFR^+$.

9. The composition according to claim 1, wherein greater than 20% of said cells are human stem cells characterized as $FGFR^+$ and either $CD34^+$ or $CD34^-lin^-$ and further having one or more markers indicative of stromal cells.

10. A composition in accordance with claim 9, wherein said marker indicative of stromal cells is $STRO-1^+$.

11. The composition according to claim 7, wherein greater than 20% of said cells are human stem cells characterized as $FGFR^+$ and either $CD34^+$ or $CD34^-lin^-$ and further having one or more markers indicative of endothelial cells.

12. The composition according to claim 6, wherein greater than 20% of said cells are human stem cells characterized as $FGFR^+$ and either $CD34^+$ or $CD34^-lin^-$ and further having one or more markers indicative of stromal cells.

13. A composition in accordance with claim 1, wherein said human stem cells are a subpopulation of peripheral blood cells, bone marrow cells, or cord blood cells.

14. The composition according to claim 1, wherein greater than 90% of said cells are human stem cells characterized as $FGFR^+$ and also having another phenotype indicative of a primitive state.

15. The composition according to claim 1, wherein greater than 90% of said cells are human stem cells characterized as $FGFR^+$ and either $CD34^+$ or $CD34^-lin^-$ and further having one or more of the markers $Thy-1^+$, $AC133^+$ and $c-kit^+$.

16. The composition according to claim 1, wherein greater than 90% of said cells are human stem cells characterized as $FGFR^+$ and either $CD34^+$ or $CD34^-lin^-$ and further having one or more markers indicative of endothelial cells.

17. A composition in accordance with claim 16, wherein said markers indicative of endothelial cells are selected from the group consisting of $TIE-1^+$, $TEK^+$, $CD31^+$, $VE-Cadherin^+$ and $VEGFR^+$.

18. The composition according to claim 1, wherein greater than 90% of said cells are human stem cells characterized as $FGFR^+$ and either $CD34^+$ or $CD34^-lin^-$ and further having one or more markers indicative of stromal cells.

19. A composition in accordance with claim 18, wherein said marker indicative of stromal cells is $STRO-1^+$.

20. The composition according to claim 6, wherein greater than 90% of said cells are human stem cells characterized as $FGFR^+$ and either $CD34^+$ or $CD34^-lin^-$ and further having one or more markers indicative of endothelial cells.

21. The composition according to claim 6, wherein greater than 90% of said cells are human stem cells characterized as $FGFR^+$ and either $CD34^+$ or $CD34^-lin^-$ and further having one or more markers indicative of stromal cells.

22. A composition in accordance with claim 14, wherein said human stem cells are a subpopulation of peripheral blood cells, bone marrow cells, or cord blood cells.

23. A cellular composition comprising a substantially homogeneous population of cultured human stem cells displaying a phenotype of $FGFR^+$ and another phenotype indicative of a primitive state, which cells are capable of giving rise to cells selected from the group consisting of endothelial cells, stromal cells and hematopoietic cells, with the proviso that said cells are not embryonic stem cells.

* * * * *